(12) United States Patent
Shibuichi et al.

(10) Patent No.: US 7,472,577 B2
(45) Date of Patent: Jan. 6, 2009

(54) HAIR SENSOR

(75) Inventors: Satoshi Shibuichi, Tokyo (JP); Shu Ahiko, Tochigi (JP); Shinji Hamamoto, Tochigi (JP); Hisashi Misumi, Tochigi (JP); Hidesato Kizaki, Tokyo (JP)

(73) Assignee: Kao Corporation, Tokyo (JP)

( * ) Notice: Subject to any disclaimer, the term of this patent is extended or adjusted under 35 U.S.C. 154(b) by 301 days.

(21) Appl. No.: 11/336,968

(22) Filed: Jan. 23, 2006

(65) Prior Publication Data

US 2006/0184068 A1    Aug. 17, 2006

(30) Foreign Application Priority Data

Jan. 24, 2005 (JP) ............................. 2005-016199

(51) Int. Cl.
*G01N 3/56* (2006.01)

(52) U.S. Cl. ............................................................ 73/9

(58) Field of Classification Search .................. 73/579, 73/9, 86, 763, 159, 160
See application file for complete search history.

(56) References Cited

U.S. PATENT DOCUMENTS 5,165,170 A * 11/1992 Sagol et al. ................. 30/34.05
2003/0233861 A1   12/2003 Woolston et al.

FOREIGN PATENT DOCUMENTS

| JP | 62-297752   | * 12/1987 |
|----|-------------|-----------|
| JP | 5-256631    |   10/1993 |
| JP | 2004-159830 |    6/2004 |
| JP | 2004-527730 |    9/2004 |
| JP | 2006-158526 | *  6/2006 |

OTHER PUBLICATIONS

William C. Waggoner, et al. "Instrumental Method for the Determination of Hair Raspiness", Journal of the Society of Cosmetic Chemists, 17, 1966, pp. 171-179.

* cited by examiner

*Primary Examiner*—Helen C. Kwok
(74) *Attorney, Agent, or Firm*—Oblon, Spivak, McClelland, Maier & Neustadt, P.C.

(57) ABSTRACT

A hair sensor, which can suppress mixing of external noise to a minimal level when a sliding sound of hair is detected, amplified, and output as an audio output in order to estimate surface characteristics and the degree of hair damage, and which can be easily used, is provided. The hair sensor for detecting the sliding sound of the hair in order to estimate hair characteristics includes a sliding element capable of sliding on the hair and a housing which includes a microphone provided therein. The sliding element is erected on a diaphragm. The sliding element and the diaphragm are arranged to allow the sliding sound caused by the sliding element to be transmitted through the diaphragm to the microphone and to attenuate vibration transmitted from outside of the diaphragm to the microphone. The surface of the sliding element is preferably treated to have a roughened surface in order to improve slidability thereof during measurement and measurement accuracy.

15 Claims, 15 Drawing Sheets

A view of an x-x cross-section

A view of an x-x cross-section

A view of an x-x cross-section

A view of an x-x cross-section

A view of an x-x cross-section

A view of an x-x cross-section

Example 1

Example 2

With low-frequency noise filter

Without low-frenquency noise filter

Sounds generated when an operator grasps the sensor | Sliding sound

HAIR SENSOR

FIELD OF THE INVENTION

The present invention relates to a sensor used for estimating characteristics of hair such as the surface condition or hardness of hair by detecting the sliding sound of the hair.

BACKGROUND OF THE INVENTION

A combing sound is generated when a comb or brush is run through a person's hair. This sound is generally louder in the case where the surface of the hair is significantly damaged. This is because the friction between the teeth of the comb or brush and the hair is greater than the case where hair is undamaged. By contrast, the combing sound is softer where a person's hair is less damaged or the surface of the hair is smoothened by a hair care product.

Given the above relationship, various systems for estimating hair characteristics such as hair damage or a change of hair condition attributable to a hair care product based on the combing sound are proposed. For example, (the publication in J. SOC. COSMETIC CHEMISTS, Vol 17, pages 171-179 (1966)) describes a device which includes a comb or brush provided with a microphone fixed at a central point of the back of the comb or brush, and a signal amplifier for amplifying a combing sound signal detected by the microphone when the comb or brush is run through a person's hair, (Published Japanese Translation No. 2004-527730 of PCT International Application) describes a device which is based on the same principle as Japanese Patent Application Laid-open No. 2004-159830 which describes a device which performs a frequency analysis of a combing sound signal by performing Fourier transform and is arranged to output the amplified combing sound signal from a speaker as an audio output.

In the above case, where the comb or brush is provided with a microphone centrally fixed at a central portion of the back of the comb or brush, when run through hair, the combing sound contains a large amount of noise from many external sources. Therefore, even if the combing sound signal detected by the microphone is amplified and converted to an audio output, it remains difficult to distinguish the combing sound from other noise sources. Therefore, estimation of the hair characteristics such as hair damage based on the combing sound output as the audio output is difficult via existing sensors.

SUMMARY OF THE INVENTION

The present invention relates to a hair sensor for detecting a sliding sound of hair in order to estimate hair characteristics including: a sliding element capable of sliding on hair; a housing including a microphone provided therein; and a diaphragm on which the sliding element is located to erect, wherein the sliding element and the diaphragm are arranged to allow a sliding sound caused by the sliding element to be transmitted to the microphone as vibration and to attenuate vibration transmitted from outside of the diaphragm to the microphone.

DETAILED DESCRIPTION OF THE INVENTION

Figure 1A:
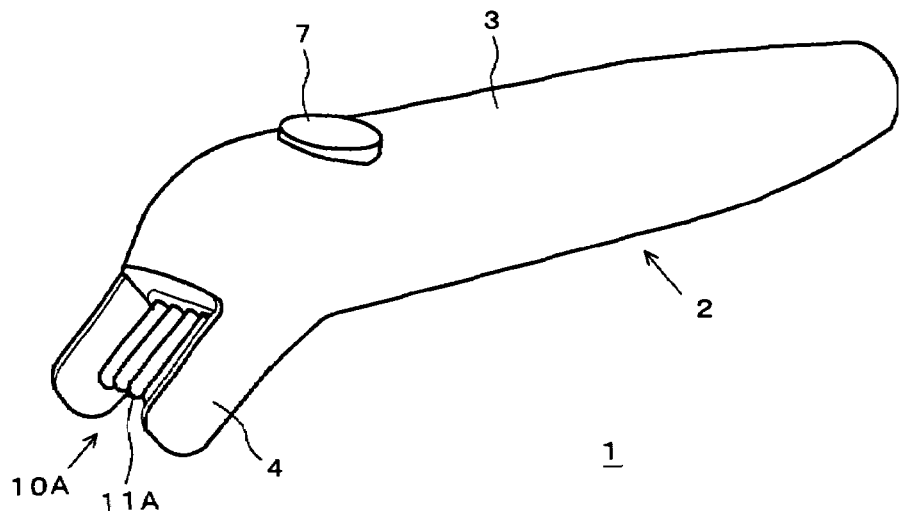
FIG. 1A is a perspective view showing the appearance of a hair sensor according to an embodiment of the present invention.

The present invention has benefits such as suppressing mixing of unwanted noise to a minimal level so as to enable the estimation of hair characteristics to be easily and accurately performed based on a sliding sound of hair detected, amplified, and output as an audio output, and ensuring ease of actual operation and maintainability. The benefits of the present invention include estimating the degree of hair damage or the change of hair condition attributable to a hair care product.

Although not wanting to be limited in theory, the inventors of the present invention found the following discoveries, as reasons that sound from many noise sources were detected together with the combing sound when a conventional comb or brush provided with a microphone was run through hair and that estimation of hair characteristics based on the combing sound was difficult: (i) The combing sound detected when the conventional comb or brush with the microphone was run through the hair could easily contain a sound generated by sliding of the teeth of the comb or brush on the scalp as noise in addition to the sound generated by sliding of the teeth of the comb or brush through the hair. (ii) Someone's voice, the driving sound of a car, in-store background music, and the like could be easily detected as noise in the case where the conventional comb or brush with the microphone was used at a store or outdoors. (iii) There was a large difference of the detection sensitivity between a sound detected when the center of the comb or brush was run through the hair and that detected when an end of the comb or brush was run through the hair, because the microphone was fixed at the center of the back of the comb or brush. (iv) It was not clear whether the detected combing sound was generated by combing with the center of the comb or brush or with the end of the comb or brush. In some cases, both the combing sounds were mixed for output. (v) Surface roughness of the sliding element that was to be run through hair affected the measurement result. (vi) When an operator grasped a comb serving as a sensor or a housing in which a sensor was provided, a large low-frequency noise was mixed. The inventors also found that, when sliding elements for detecting a sliding sound of hair were located to erect on a diaphragm in such a manner that no sliding elements were erected outside the diaphragm, instead of teeth of a comb or brush conventionally used, the sliding element and the diaphragm were arranged at a position at which a high sensitivity of the microphone was obtained. This configuration can reduce vibration transmitted without passing through the diaphragm to the microphone as well as suppressing noise detection, enabling the sliding sound of the hair to be detected in a desirable manner. Moreover, the inventors further found that measurement accuracy could be improved by providing fine roughness on the surface of a sliding element and the sliding sound of the hair could be detected in a good manner by adding a noise filter for cutting low frequency components. Based on the above findings, the inventors completed the present invention.

The hair sensor of the present invention has a sliding element that can slide on hair and is located on a diaphragm. The sliding element and the diaphragm are arranged at a high-sensitivity site, e.g., a position immediately adjacent a diaphragm of a microphone, thereby allowing a sliding sound caused by the sliding element to be efficiently transmitted to the microphone as vibration and attenuating vibration transmitted from outside of the diaphragm (in other words, without passing through the diaphragm) to the microphone. Thus, the microphone can mainly detect the sliding sound caused by direct sliding of the sliding element on the hair. Namely, this can suppress the detection of a sound generated by sliding of the teeth of a comb or brush on the hair outside a range of directivity of the microphone or a sound generated by sliding of the teeth of the comb or brush on a scalp as a noise.

Therefore, it is possible to easily and accurately estimate hair characteristics by amplifying a signal detected by the above hair sensor and outputting the amplified signal as an audio output or by displaying a sound signal on a monitor in a visual manner.

BRIEF DESCRIPTION OF THE DRAWINGS

The present invention is now described in detail, with reference to the drawings. In the drawings, the same reference numerals represent the same or equivalent components.

Figure 1B:
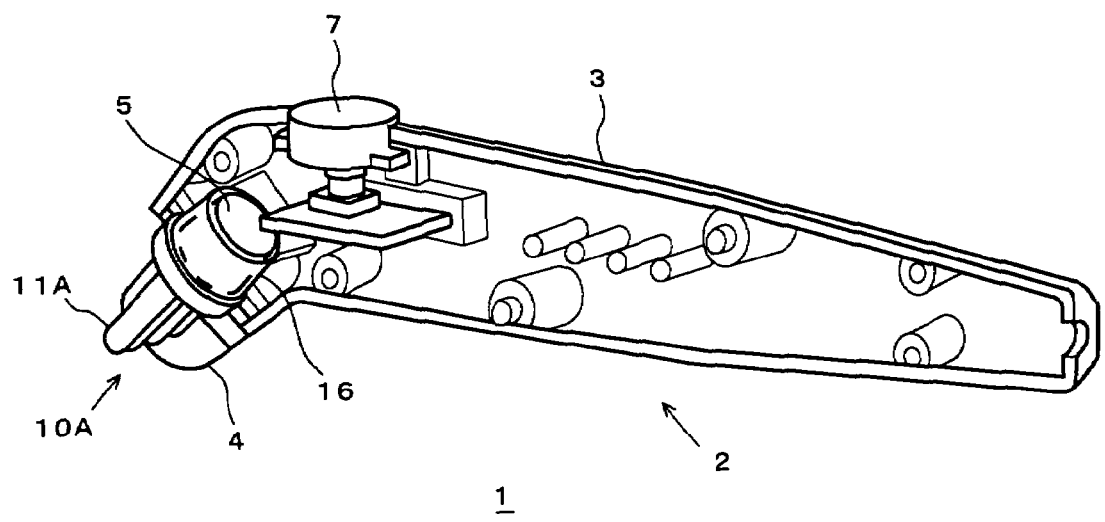
FIG. 1B is a perspective view showing the internal structure of the hair sensor according to an embodiment of the present invention.

FIG. 1A is a perspective view showing the appearance of a hair sensor 1 according to one embodiment of the present invention. FIG. 1B is a perspective view showing the internal structure of the hair sensor 1.

The hair sensor 1 detects the sliding sound of hair in order to estimate hair characteristics, e.g., the arranged condition of cuticles, the surface condition such as unevenness of the surface of the hair, hardness, and tangling of the hair. The hair sensor 1 includes a housing 2 provided with a sliding unit 10A.

A central part of the housing 2 serves as a gripping portion 3. The housing 2 is angled or angulated around an upper portion top end into which the sliding unit 10A is detachably attached. A guard member 4 is formed integrally with the housing 2 at both ends of the sliding unit 10A. A microphone 5 is provided inside the housing 2 located adjacent to the sliding unit 10A. A switch 7 to operate the microphone 5 is provided on a surface of the housing 2.

Figure 2A:
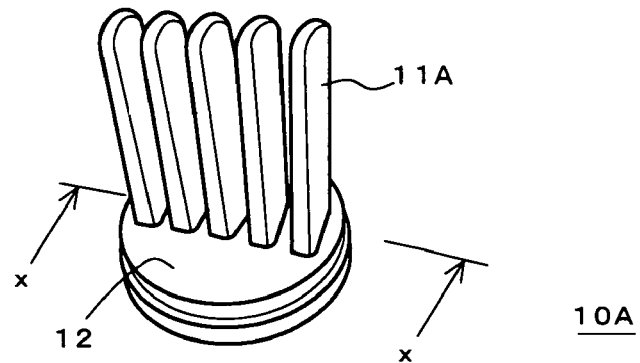
FIG. 2A is a perspective view of a sliding unit 10A.
Figure 2B:
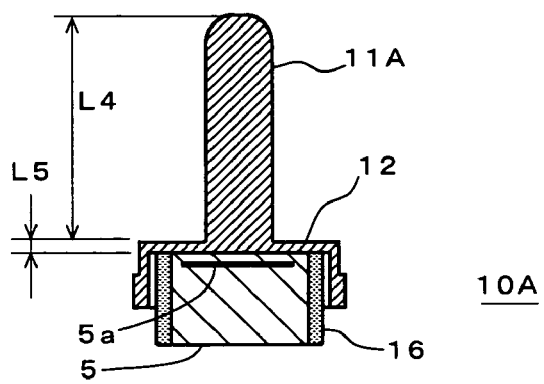
FIG. 2B is a cross-sectional view of the sliding unit 10A.
Figure 2C:
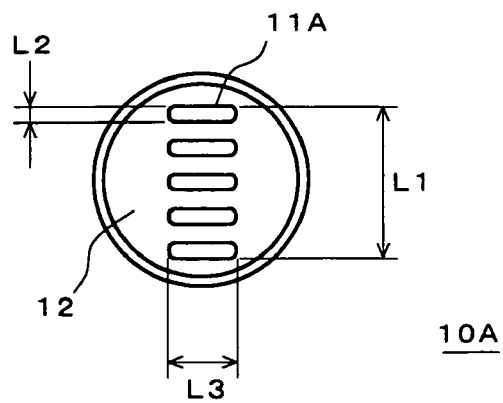
FIG. 2C is a top view of the sliding unit 10A.

As shown in FIGS. 2A, 2B, and 2C, a plurality of sliding elements 11A in the form of flat bars are arranged to erect out from a diaphragm 12 in the sliding unit 10A. In this preferred embodiment, the diaphragm 12 is located immediately adjacent a diaphragm 5a of the microphone 5, more preferably, within 10 mm ahead of the diaphragm 5a of the microphone 5. Preferably, there are no obstacles for sound transmission between the diaphragm 12 and the microphone 5 so as to allow efficient transmission of sound vibration from the diaphragm 12 to the microphone 5. In the above embodiment, it is preferable that the diaphragm 12 on which the flat-bar-like sliding elements 11A are erected is located as closely to the diaphragm of the microphone 5 as possible or is located so as to be in direct contact with the diaphragm of the microphone 5, in accordance with the structure of the microphone 5 used in the hair sensor 1. The diaphragm 12 may be formed integrally with the diaphragm of the microphone 5. When the microphone 5 is an electric condenser type microphone in which a diaphragm 5a is arranged back from a front face of the microphone 5, it is preferable to bond the front face of the microphone 5 to the diaphragm 12 of the sliding element with a double-sided adhesive tape, a liquid glue or the like so as to locate the diaphragm 5a as closely to the diaphragm 12 as possible, as shown in FIG. 2B.

Alternatively, when the microphone 5 is a piezoelectric microphone including a piezoelectric device, the microphone is preferably arranged in such a manner that the diaphragm of the microphone that is exposed on the front face thereof is in direct contact with the diaphragm 12 of the sliding element or is located as closely to the diaphragm 12 as possible.

The present embodiment also includes the feature of flat-bar-like sliding elements 11A and the diaphragm 12 being arranged so as to attenuate undesirable vibration noise transmitted from outside of the diaphragm 12 to the microphone 5. More specifically, the diaphragm 12 and the flat-bar-like sliding elements 11A extending from the diaphragm 12 are arranged at a position immediately adjacent the diaphragm of the microphone 5 where sensitivity is relatively high, in such a manner that no flat-bar-like sliding elements 11A extend outside the diaphragm 12. Using this arrangement, a high sensitivity is achieved.

It is also preferable that, except for a minimum space required for arranging a switch, a printed circuit board, or the like, the inside of the housing 2 is filled with a plastic material so as to prevent resonance of the housing 2 and the diaphragm 12 is arranged within that housing 2. This arrangement has been found to also assist in attenuating noise transmitted from the outside of the diaphragm 12 to the microphone 5.

In order to attenuate vibrations from the outside of the diaphragm 12 to the microphone 5, it is preferable to surround the microphone 5, except for the side of the microphone 5 directly facing the diaphragm 12, with a vibration attenuator 16 selected from natural rubbers, synthetic rubbers, foam materials, synthetic resins having a sound insulating property, and the like. Preferably, the microphone 5 is surrounded with the vibration attenuator 16 made of silicone rubbers.

A length L1 of the arrangement of the flat-bar-like sliding elements 11A is preferably in a range from 4 to 25 mm, so that the length L1 may be shorter than the length of a typical comb or brush. Due to the size of length L1, it is possible to run all of the erecting flat-bar-like sliding elements 11A through the hair simultaneously when detecting the hair sliding sound, thereby making the detection sensitivity stable.

Each flat-bar-like sliding element 11A preferably has a thickness L2 in a range from 0.5 to 3 mm, a width L3 in a range from 1 to 15 mm, and a height L4 in a range from 5 to 25 mm in order to reduce friction resistance when the sliding element 11A slides through hair therefore minimizing additional noise, and more preferably has a height L4 in a range from 5 to 15 mm in order to secure mechanical strength.

Preferably, the flat-bar-like sliding element 11A is made from a material with sufficient mechanical strength to be able to endure repeated use as well as repeated cleaning and sterilization processes using organic solvents such as alcohol. This is important to allow the hair sensor 1 to be used repeatedly to measure the hair characteristics for many people. Preferred materials for the flat-bar-like sliding element 11A include metals such as duralumin, aluminum, stainless steel, iron, copper, and associated metal alloys. On the other hand, if the flat-bar-like sliding element 11A is formed from a polymer material such as high-density polyethylene, the material strength is not sufficient. As a result, the sliding element 11A may break when repeatedly used for estimation of customer's hair outside or at the store. Moreover, the flat-bar-like sliding element formed from the polymer material may be broken, when repeatedly cleaned with organic solvents such as alcohol in order to remove hair care products such as a styling product that adheres to the sliding element.

It is hard for the flat-bar-like sliding element 11A having a too smooth surface to generate a sufficient level of the sliding sound. Moreover, especially long hair can be easily entangled with the sliding element 11A having a too smooth surface. On the other hand, when the surface of the flat-bar-like sliding element 11A is too rough, hair can be easily entangled with the sliding element 11A. Thus, it is preferable to make the surface of the flat-bar-like sliding element 11A rough properly. More specifically, the surface roughness Ra of the flat-bar-like sliding element 11A is preferably 0.1 µm or more and 5.0 µm or less, and more preferably 0.5 µm or more and less than 2.5 jim by sandblasting, anodization, chemical treatment, electric discharging, cutting, a combination of two or more treatments above, and the like.

The flat-bar-like sliding elements 11A are arranged in a line erecting in the thickness direction of the flat-bar-like sliding element 11A in the sliding unit 10A. The sliding elements may be arranged in multiple lines. However, a single-line arrangement is preferable because the sliding sound can be accurately detected. This is because, where the elements are arranged in multiple lines, overlapping of a sliding sound generated by the front row and a sliding sound generated by the back row may occur during detection of the sliding sound of the hair, therefore lowering the sensing accuracy.

It is preferable that the diaphragm 12 is thin in order to improve the detection sensitivity. However, when the diaphragm 12 is too thin, the strength thereof is low and the diaphragm 12 can easily be broken. By contrast, when the diaphragm 12 is too thick, detection sensitivity is low. Therefore, the thickness L5 of the diaphragm 12 is preferably in the range from 0.1 to 4 mm, and more preferably in the range from 0.1 mm.

When the flat-bar-like sliding elements 11A and the diaphragm 12 are formed separately from each other and then the flat-bar-like sliding elements 11A are embedded into and fixed to the diaphragm 12, it is difficult to form the diaphragm 12 to have a thickness of the above range. Therefore, it is preferable to monoblock-mold the flat-bar-like sliding elements 11A and the diaphragm 12 by machining of metals.

Examples of the microphone 5 that may be used in the present invention include a condenser type, a piezoelectric type, and a dynamic type. A condenser type microphone is preferable because it can be made to be compact, has flat frequency characteristics over a wide frequency band, and has high stability. Preferably, the microphone 5 is cardioid in view of suppressing noise.

In the hair sensor 1, the guard member 4 on both sides of the flat-bar-like sliding elements 11A is formed so as to project from the flat-bar-like sliding elements 11A when the sliding unit 10A is mounted on the microphone 5 in the housing 2. Thus, the flat-bar-like sliding elements 11A do not come into contact with the examinee's scalp, even when the sliding unit 10A of the hair sensor 1 is run through hair in the same manner as that of combing of hair with a typical comb. As a result of avoiding scalp contact, it is possible to prevent a sliding sound from the scalp from being mixed as noise into the sliding sound of the hair.

Figure 3A:
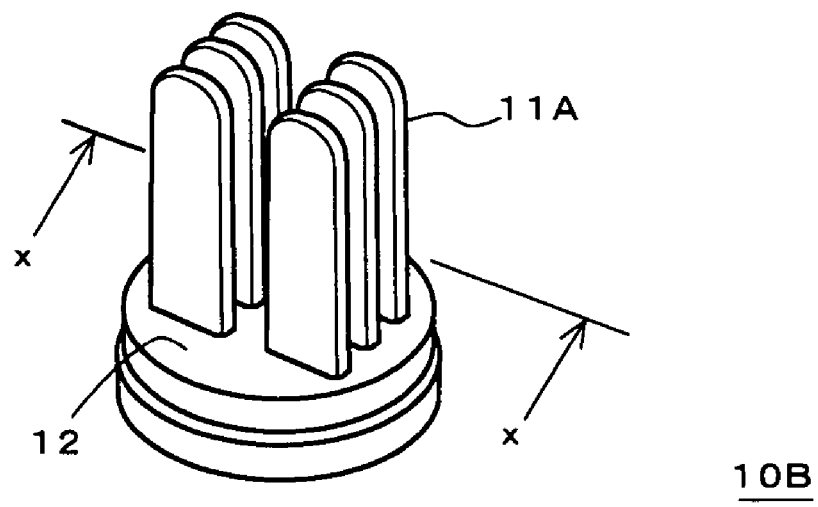
FIG. 3A is a perspective view of a sliding unit 10B.
Figure 3B:
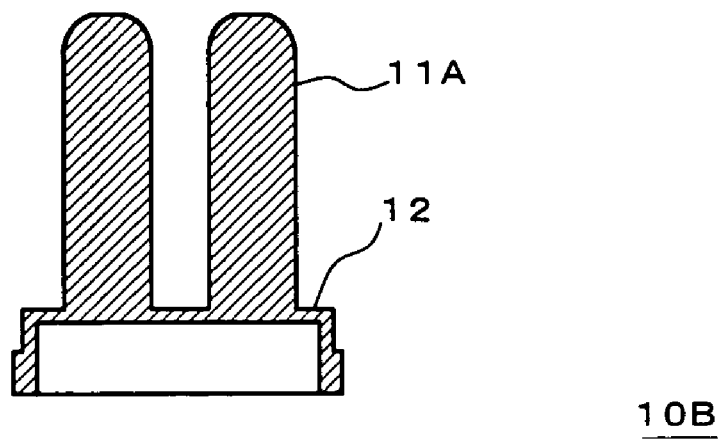
FIG. 3B is a cross-sectional view of the sliding unit 10B.

The hair sensor 1 can be formed in various configurations. For example, instead of the aforementioned sliding unit 10A in which the flat-bar-like sliding elements 11A are arranged in a line, a sliding unit 10B may be formed wherein the flat-bar-like sliding elements 11A are arranged in two lines, as shown in FIGS. 3A and 3B, and the sliding unit 10B is then attached to the housing 2.

Figure 4A:
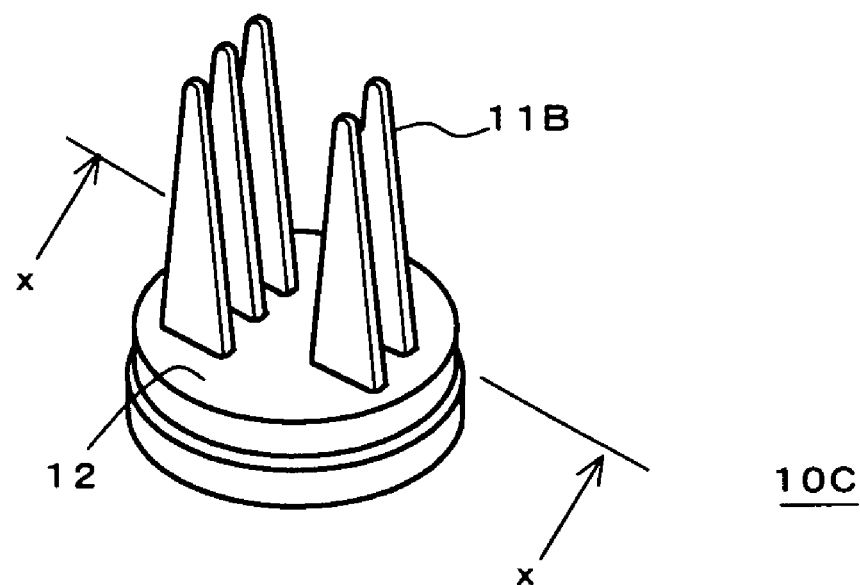
FIG. 4A is a perspective view of a sliding unit 10C.
Figure 4B:
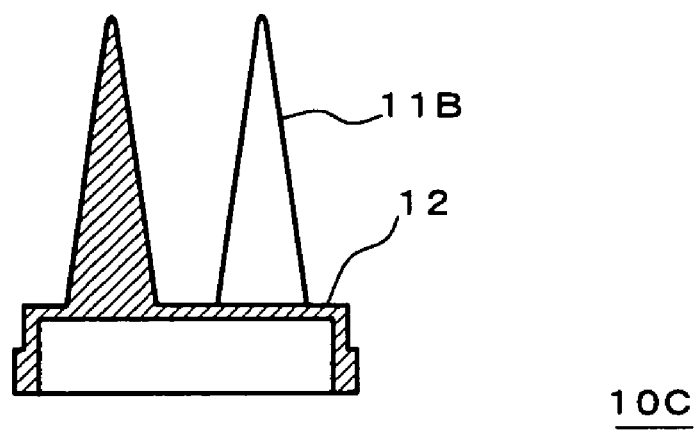
FIG. 4B is a cross-sectional view of the sliding unit 10C.

Alternatively, the flat-bar-like sliding element 11A may be replaced with a triangular-plate-like sliding element 11B in a sliding unit 10C as shown in FIGS. 4A and 4B. The triangular-plate sliding elements 11B may be arranged in such a manner-like that sliding elements in the first row and those in the second row are arranged in a staggered manner.

Figure 5A:
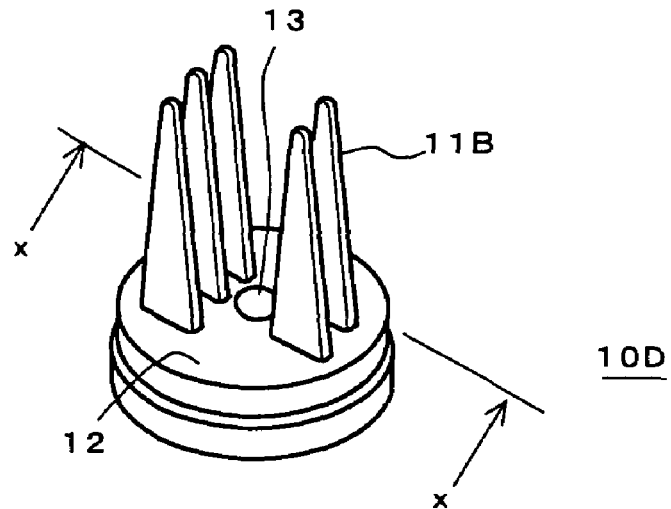
FIG. 5A is a perspective view of a sliding unit 10D.
Figure 5B:
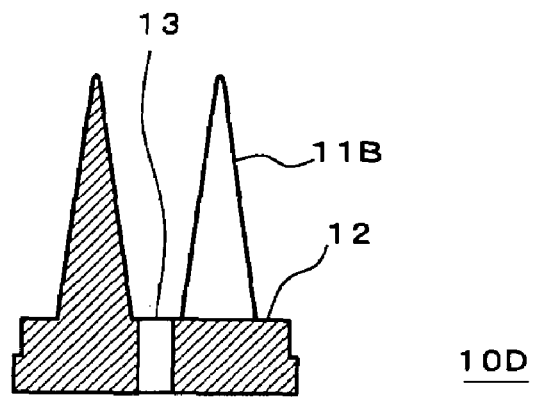
FIG. 5B is a cross-sectional view of the sliding unit 10D.

In addition, despite the sliding element being flat-bar-like or triangular-plate-like, the diaphragm 12 may be formed to be thick and include a hole 13 formed therein as in a sliding unit 10D shown in FIGS. 5A and 5B, if necessary. The sliding sound of the hair is detected by the microphone 5. According to this sliding unit 10D, not only the sliding sound generated by sliding of the sliding elements on the hair but also a sliding sound generated by sliding between strands of hair can be detected. However, the level of external noise is larger compared with the sliding unit 10C shown in FIGS. 4A and 4B.

Figure 6:
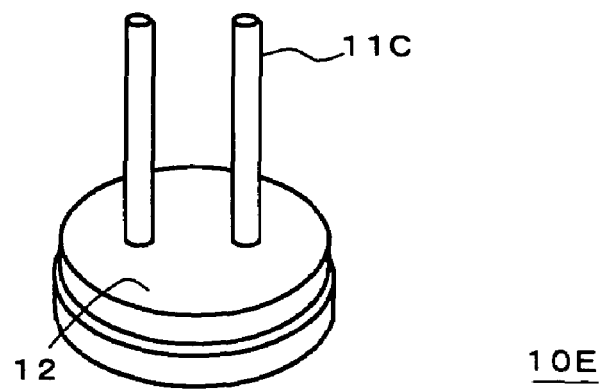
FIG. 6 is a perspective view of a sliding unit 10E.
Figure 7:
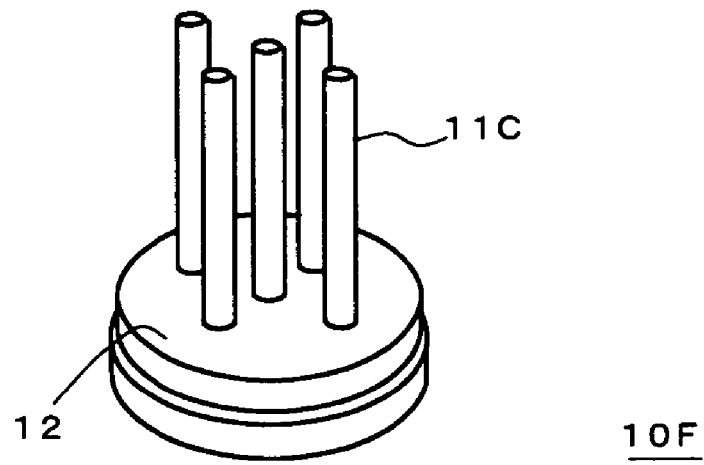
FIG. 7 is a perspective view of a sliding unit 10F.

Moreover, round-bar-like sliding elements 11C may be used as in a sliding unit 10E shown in FIG. 6. The round-bar-like sliding elements 11C may be arranged crisscross as in a sliding unit 10F shown in FIG. 7.

The flat-bar-like sliding element 11A, the triangular-plate-like sliding element 11B, and the round-bar-like sliding element 11C are compared with one another as below.

In the case of the triangular-plate-like sliding element 11B, a portion thereof near to the diaphragm 12 is different from an edge thereof far from the diaphragm 12 with respect to a contact area of hair with the sliding element, and the detection sensitivity of the sliding sound varies according to a contact position of hair with the sliding element. To the contrary, in the case of the flat-bar-like sliding element 11A, the detection sensitivity of the sliding sound is hardly affected by the contact position of hair with the sliding element, which is preferable. Comparing the roundbar-like sliding element 11C with the flat-bar-like sliding element, the flat-bar-like sliding element 11A can preferably detect the sliding sound more effectively than the round-bar-like sliding element 11C, since the contact area of hair with the flat-bar-like sliding element 11A is larger than that with the round-bar-like sliding element 11C.

In any of the above embodiments, it is preferable to provide a low-frequency noise filter that can suppress low-frequency noise components having frequencies of 100 Hz or less in a transmission path of the signal detected by the microphone 5. More specifically, in many cases, a change in the grasping force applied to the housing 2 of the hair sensor 1 is detected as a low-frequency noise having a frequency of 100 Hz or less when an operator grasps or releases the housing 2 of the hair sensor 1 or during a measurement. The level of this low-frequency noise is relatively large. Therefore, this low-frequency noise affects the measured signal. On the other hand, according to the present invention, the low-frequency noise filter provided in the signal transmission path of the signal detected by the microphone 5 can remove the above low-frequency noise.

Examples of the low-frequency noise filter include an n-th filter including a capacitor and a resistance, an active filter using a logic operator, and the like. In general, a decoupling capacitor is series connected between a microphone and an amplifier circuit and is set to allow signal components with frequencies in an audible range to pass therethrough. Therefore, the low-frequency noise components generated by gripping the housing 2 of the hair sensor 1 or the like can pass through the decoupling capacitor. The low-frequency noise filter can cut off those low-frequency noise components.

Preferably, the low-frequency noise filter has a filtering effect of approximately −12 db or more, and more preferably approximately −20 db or more for frequencies of 50 Hz or less. For frequencies of 300 Hz or more, the low-frequency noise filter preferably has a loss of 0 dB, and more preferably a loss within approximately −3 db.

The low-frequency noise filter may be incorporated into the hair sensor 1 or be provided on a former stage of the amplifier circuit to which the hair sensor 1 is connected, in accordance with the form of the low-frequency noise filter.

Figure 8:
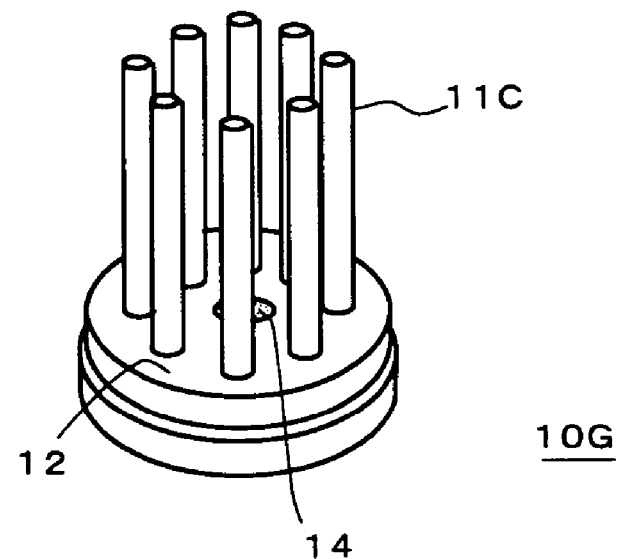
FIG. 8 is a perspective view of a sliding unit 10G.

An optical displacement measurement sensor 14 that is the same type as that used in an optical mouse may also be used as in a sliding unit 10G shown in FIG. 8, so that the detected sliding sound is analyzed while being associated with the relative displacement of the sliding element with respect to the hair. Alternatively, a strain gauge 15 in the form of a film and the microphone 5 may be attached to the back of the diaphragm 12 as in a sliding unit 10H shown in FIGS. 9A and 9B. In this case, when the sliding unit 10H is run through hair, a load applied to the hair can be detected together with the sliding sound. In this manner, the condition of the hair can be analyzed in more detail.

Furthermore, two planar sliding elements opposed to each other may be used instead of the sliding unit in which the sliding elements in the form of bars are erected on the diaphragm. In this case, the two sliding elements are run through hair while sandwiching the hair therebetween, thereby obtaining the sliding sound of the hair (not shown).

Figure 9A:
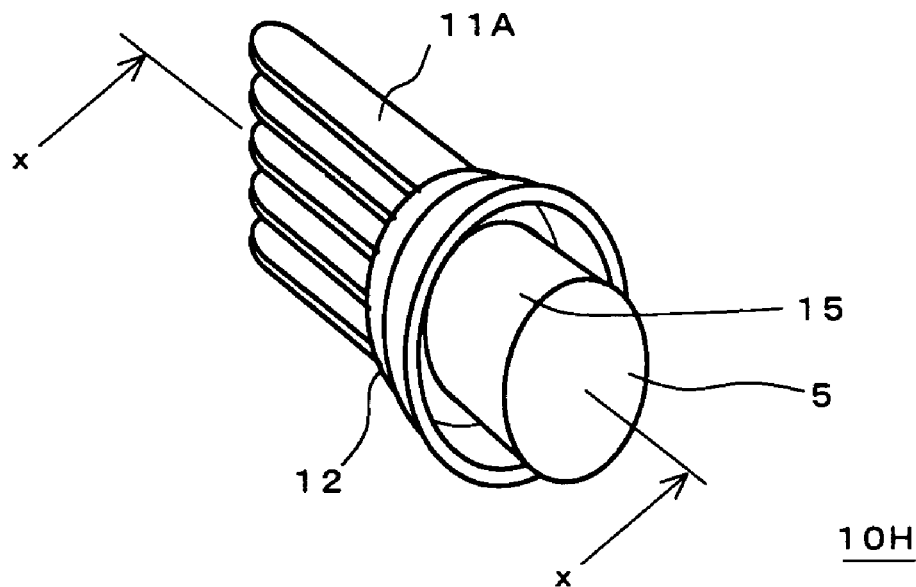
FIG. 9A is a perspective view of a sliding unit 10H.
Figure 9B:
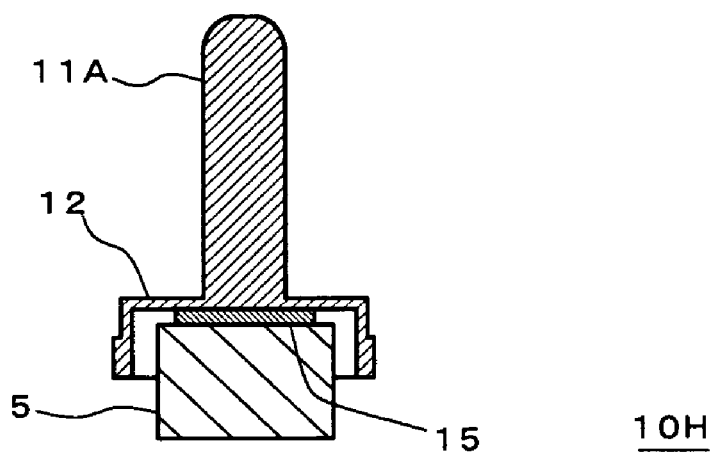
FIG. 9B is a cross-sectional view of the sliding unit 10H.

As shown in FIGS. 9A and 9B, when the strain gauge 15 is attached, the strain gauge 15 should be bonded to the diaphragm 12 together with the microphone 5. This is because of obtaining the sliding sound and strain signals from the same portion of the hair in a synchronized manner. When the strain gauge 15 is provided on a position separate from the microphone 5, signals from the same portion of the hair are not always analyzed, causing unreliability in interpretation of the analysis results. When the strain gauge 15 and the microphone 5 are both adhered to the diaphragm 12, the hair surface conditions mainly reflect the sliding sound detected by the microphone 5, and tangling of the hair mainly reflects load detected by the strain gauge 15.

In case of the hair such that a large load is detected by the strain gauge 15, split ends or breakage of hair can easily occur because of daily brushing. Therefore, it is possible to find a site at which split ends or breakage of hair can easily occur by measuring the load. In case of a relatively small load although the sliding sound is great, it can be predicted that the hair is being cared for everyday although the hair is remarkably damaged. In case of a relatively large load although the sliding sound is low, it can be predicted that the hair is incompletely cared although the hair is not damaged.

Figure 10A:
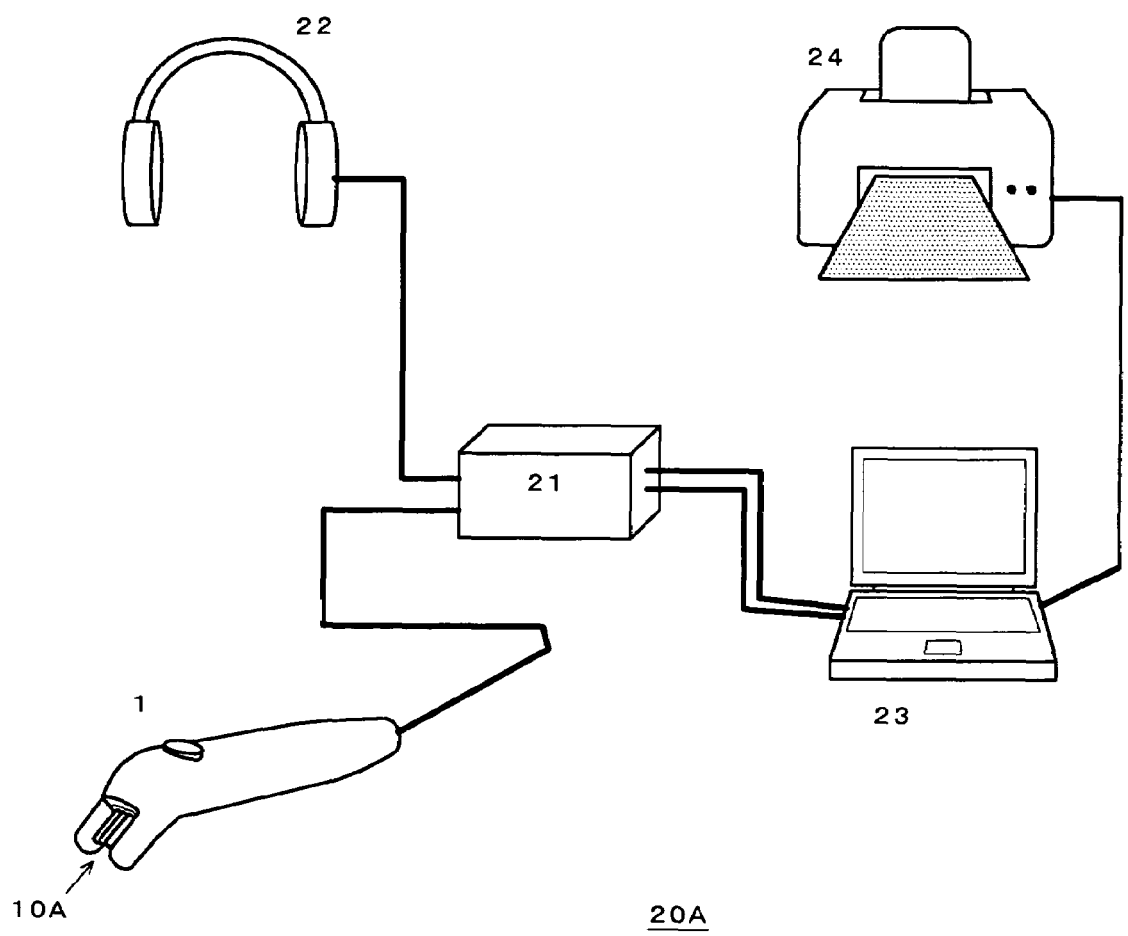
FIG. 10A shows the configuration of a system for detecting the sliding sound of hair.

The hair sensor 1 of the present invention can be used in a system 20A for detecting the sliding sound of hair as shown in FIG. 10A, for example. This detection system 20A includes: the hair sensor 1; an amplifier 21 that amplifies a signal of the sliding sound detected by the hair sensor 1, outputs the amplified signal, and adjusts the sensitivity; a headphone 22 connected to the amplifier 21; a personal computer 23 connected to the amplifier 21; and a printer 24 connected to the personal computer 23.

Figure 10B:
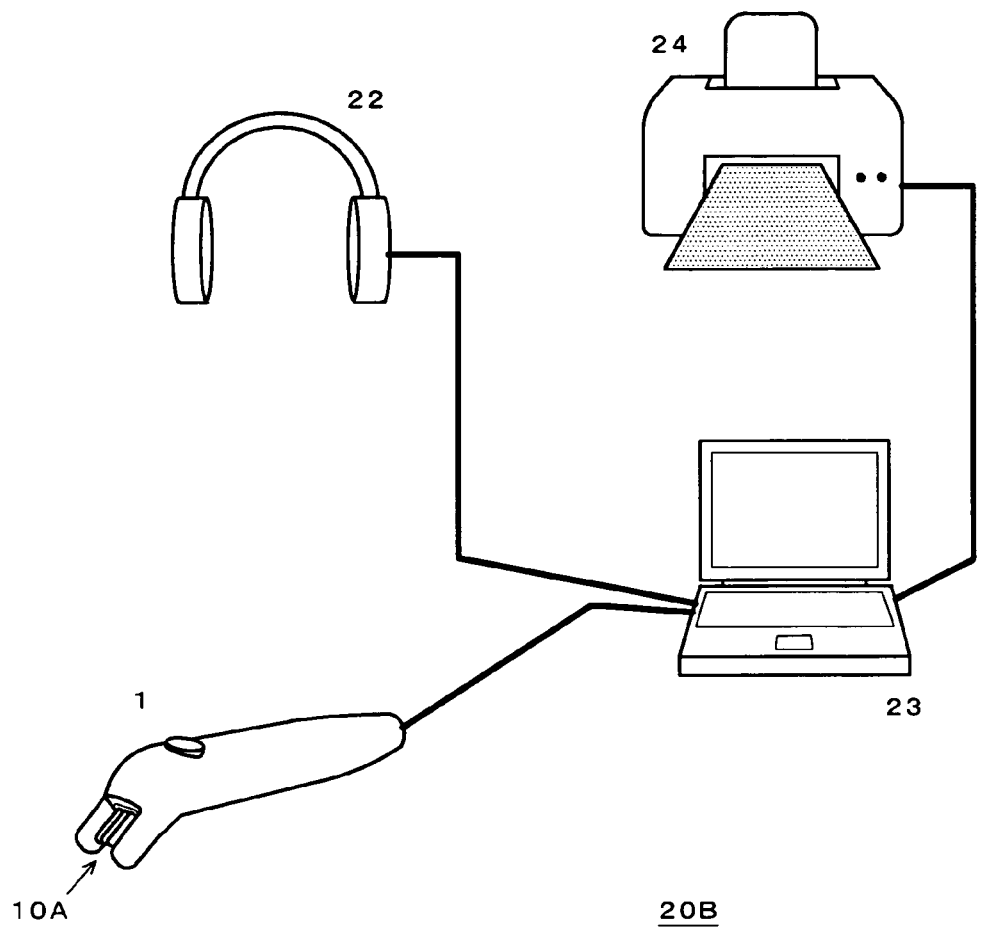
FIG. 10B shows the configuration of a system for detecting the sliding sound of hair.

Moreover, the hair sensor 1 may be directly connected to the personal computer 23 via a general purpose interface bus such as USB (Universal Serial Bus) without using the amplifier 21 in order to improve ease when used, as in a detection system 20B shown in FIG. 10B. In this case, an existing LSI that is commercially available from various companies can be used as an amplifier circuit and a USB interface circuit. Such a LSI can be incorporated into the hair sensor 1.

When the hair sensor 1 is arranged to be connectable to the personal computer 23 by USB connection, it is possible to readily use any of a broad range of general personal computers like connection of a mouse to the personal computer 23 without worrying about a difference of sensitivity of analog signal detection between models or individual machines. The amplifier circuit and the USB interface circuit can be formed by CM108 or another LSI device having functions equivalent to those of CM108 that are available from C-Media Electronics Inc., microcomputer chips H8 series available from Renesas Technology Corp., one-chip microcomputers PIC series available from Microchip Technology Inc., or microcomputer chips Easy USB series available from Cypress Semiconductor Corporation, or a combination of any of the above devices and an LSI for USB connection such as FTDI 245 series and FTDI 232 series available from Future Technology Devices International Ltd.

In the case of detecting the sliding sound of the hair by the system 20A, the sliding unit 10 of the hair sensor 1 is run through the hair to detect the sliding sound. The signal of the thus detected sliding sound is sent to the amplifier 21 (or the amplifier circuit incorporated in the hair sensor). Thus, it is possible to increase the volume and audibly hear the sliding sound of the hair via the headphone 22. In this manner, it is possible to clearly distinguish a change in the sliding sound caused by the hair characteristics, e.g., a change in the sliding sound between a condition where the hair is damaged and a condition where the damage of the hair is relieved, and a change in the sliding sound between stiff hair and soft hair. Moreover, it is possible to visually recognize the change in the sliding sound caused by the hair characteristics by displaying a relationship between frequencies and a sound level of the detected sliding sound, a relationship between a sliding time and the level of the detected sliding sound, and the like in a visual manner on a display on the personal computer 23. In the case of using the personal computer 23, hair characteristics may be estimated using several scales in accordance with the frequency and the level of the detected sliding sound. Those scales can be obtained by detecting sliding sounds for various types of hair that have known characteristics and accumulating a relationship between the characteristics and the sliding sounds in advance.

The following examples further describe and demonstrate embodiments of the present invention. The examples are given only solely for the purpose of illustration and are not to be construed as limitations of the present invention.

EXAMPLES

Example 1 and Comparative Example 1

Figure 11:
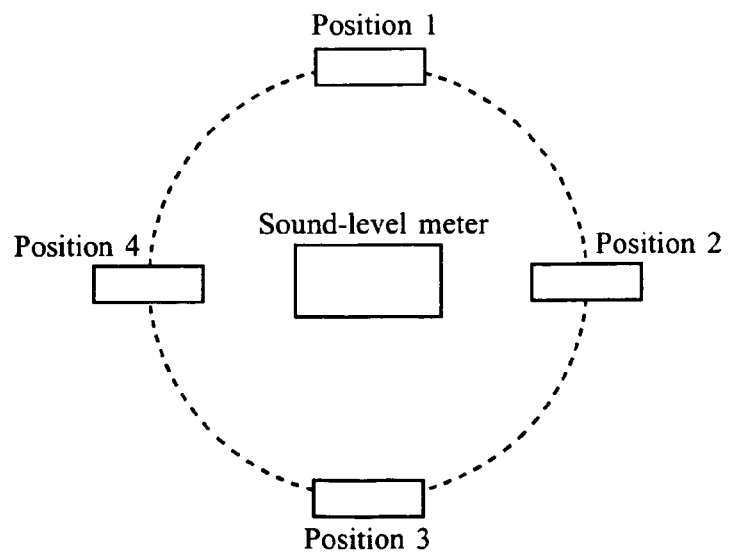
FIG. 11 shows an illustration of experiments for obtaining a relationship between a position of an electronic buzzer and measured sound volume.

(1) Relationship Between the Position of an Electronic Buzzer and Measured Sound Level In a laboratory (noise level: 48 to 50 dB), a sound-level meter (SL-1370, CUSTOM Inc) was placed at a center of a circle having a radius of 50 cm, as shown in FIG. 11. Electronic buzzers (frequency: about 2 kHz) were sequentially sounded at four respective positions (Positions 1 to 4) on that circle which surrounded the sound-level meter, and the sound level was measured by means of the sound-level meter. Table 1 shows the measurement results. As shown in Table 1, the measured sound level of the buzzer was about 80 dB. This measured sound level is close to a level measured at a 5 to 10 m point away from a road at an intersection of a six-lane road in Tokyo (70 to 80 dB).

TABLE 1

|  | Position | | | |
|---|---|---|---|---|
|  | 1 | 2 | 3 | 4 |
| Sound level of buzzer | 86 | 77 | 79 | 83 |

Unit: dB (2) Fabrication of a Hair Sensor and Measurement of a Noise from Outside A hair sensor shown in FIGS. 1A and 1B (Example 1) and a conventional hair sensor provided with a microphone centrally fixed at the back of a typical comb (Comparative Example 1) were fabricated. Each of those hair sensors was placed at the position of the sound-level meter shown in FIG. 11, and the electronic buzzers were sequentially sounded at Positions 1 to 4 in the same manner as that in (1). The sound level of the buzzer detected by each hair sensor was measured.

In this experiment, the same condenser type microphone (WM-55A103, Panasonic) was provided in each of the hair sensors of Example 1 and Comparative Example 1.

A sliding unit of the hair sensor of Example 1 had a shape shown in FIGS. 2A to 2C. The flat-bar-like sliding element of the sliding unit had a thickness L2 of 1.2 mm, a width L3 of 4.6 mm, and a height L4 of 15 mm. The flat-bar-like sliding elements were arranged in one line having a length L1 of 11 mm. The flat-bar-like sliding element was formed of duralumin (surface roughness Ra=0.7 μm). The comb of the hair sensor of Comparative Example 1 was formed of a plastic material and had teeth each of which had a height of 20 mm, a width of 2.5 mm, and a thickness of 1 mm and which were arranged in one line having a length of 100 mm.

Figure 12A:
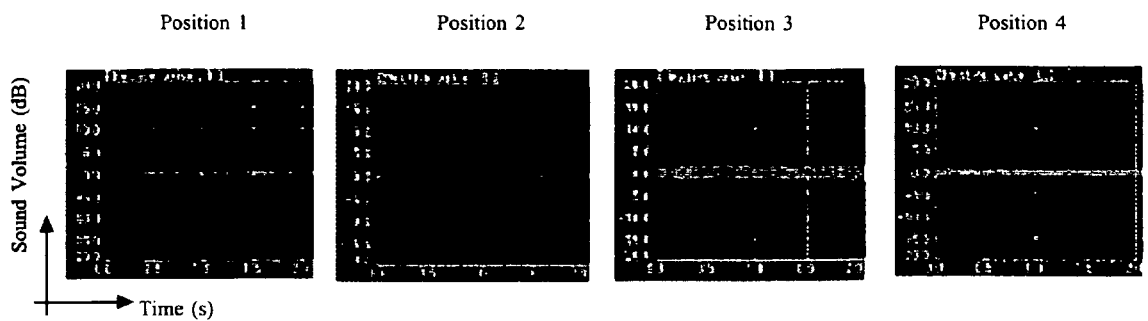
FIG. 12A is a graph of the sound volume of the buzzer detected by a hair sensor of Example 1.
Figure 12B:
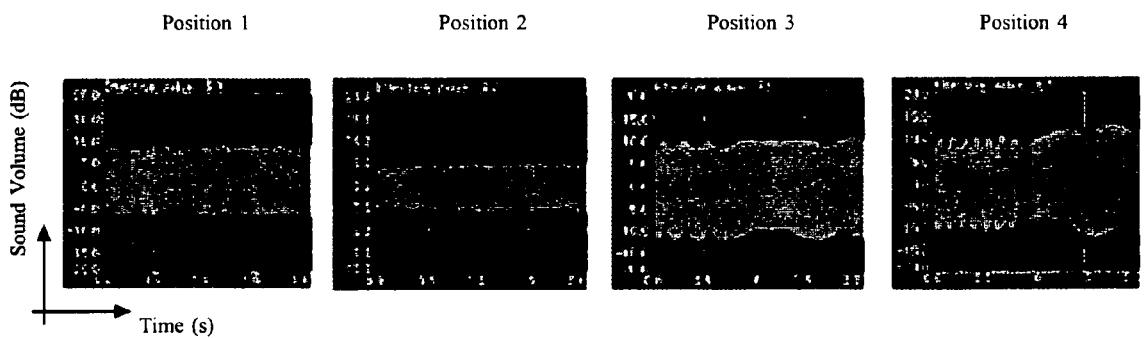
FIG. 12B is a graph of the sound volume of the buzzer detected by a hair sensor of Comparative Example 1.

Table 2 and FIGS. 12A and 12B show the sound level of the buzzer detected by each hair sensor.

TABLE 2

| Sound level detected by hair sensor (Unit: dB) | | | | |
|---|---|---|---|---|
|  | Position | | | |
|  | 1 | 2 | 3 | 4 |
| Example 1 | 1 | 1.5 | 3.5 | 2 |
| Comparative Example 1 | 17 | 11 | 24 | 25 |

Table 2 and FIGS. 12A and 12B show that a noise transmitted from the outside was reduced to a smaller level in the hair sensor of Example 1 as compared with the hair sensor of Comparative Example 1. Therefore, the hair sensor of Example 1 can provide information about friction on the surface of hair in more detail by increasing an amplification ratio. Moreover, the hair sensor of Example 1 can be used in PR events for hair care products or the like outside, especially without worrying about ambient sounds.

Example 2(2-1 to 2-7)

(1) Fabrication of Sliding Elements

Hair sensors were fabricated in the same manner as that in Example 1, except that the surface roughness of the flat-bar-like sliding elements in each hair sensor was adjusted by mirror finish or a blasting treatment to a value shown in Table 3. The surface roughness was measured by SURFCOM 590A (Tokyo Seimitsu Co., Ltd.). A measurement condition was set as follows: a length for which the measurement was performed was 1 to 3 mm, a measurement rate was 0.3 mm/s, a cut-off wavelength was 0.8 mm, a cut-off filter type was 2CR, and slope correction was performed using a least square line.

(2) Surface Roughness of a Sliding Element and Ease of Tangle of Hair

A hair bundle of clean straight hair (i.e., hair for which a chemical treatment such as a perm or color treatment was not performed) of an Asian having a length of 20 cm, a width of 2 cm, and a thickness of 0.5 cm was prepared as a hair sample. Each of the hair sensors fabricated in (1) was run through the hair sample from a root to an end. Ease of tangling of hair and a level of the hair damage caused by measurements were estimated as follows. Table 3 shows the estimation results.

Estimation of ease of tangling of hair:
Grade A: No tangling occurred from the root to the end.
Grade B: Tangling of hair occurred halfway to the end.
Grade C: Tangling of hair occurred from the beginning.
Estimation of hair damage:
Grade A: No hair surface was scraped. Grade B: A little hair surface was scraped.
Grade C: A lot of hair surface was scraped.

TABLE 3

|  | Example | | | | | | |
|---|---|---|---|---|---|---|---|
|  | 2-1 | 2-2 | 2-3 | 2-4 | 2-5 | 2-6 | 2-7 |
| Surface roughness | 0.1 μm (Mirror finish) | 0.7 μm (Blast treatment after alumite treatment) | 0.8 μm (Blast treatment after alumite treatment) | 1.4 μm (Blast treatment after alumite treatment) | 2.4 μm (Blast treatment after alumite treatment) | 2.5 μm (Blast treatment after alumite treatment) | 8.7 μm (Blast treatment after alumite treatment) |

TABLE 3-continued

|  | Example | | | | | | |
| --- | --- | --- | --- | --- | --- | --- | --- |
|  | 2-1 | 2-2 | 2-3 | 2-4 | 2-5 | 2-6 | 2-7 |
| Tangling of hair | B | A | A | A | B | C | C |
| Hair damage | A | A | A | A | A | B | C |

When the surface roughness of the sliding element was 2.5 µm or more, hair was entangled with the sliding elements from the beginning and was therefore damaged, as shown in Table 3. On the other hand, when the surface of the sliding element was mirror-finished, tangling of hair did not occur at first. However, tangling of hair then occurred and the sliding elements could not be run through the hair to the end in some cases.

Figure 13:
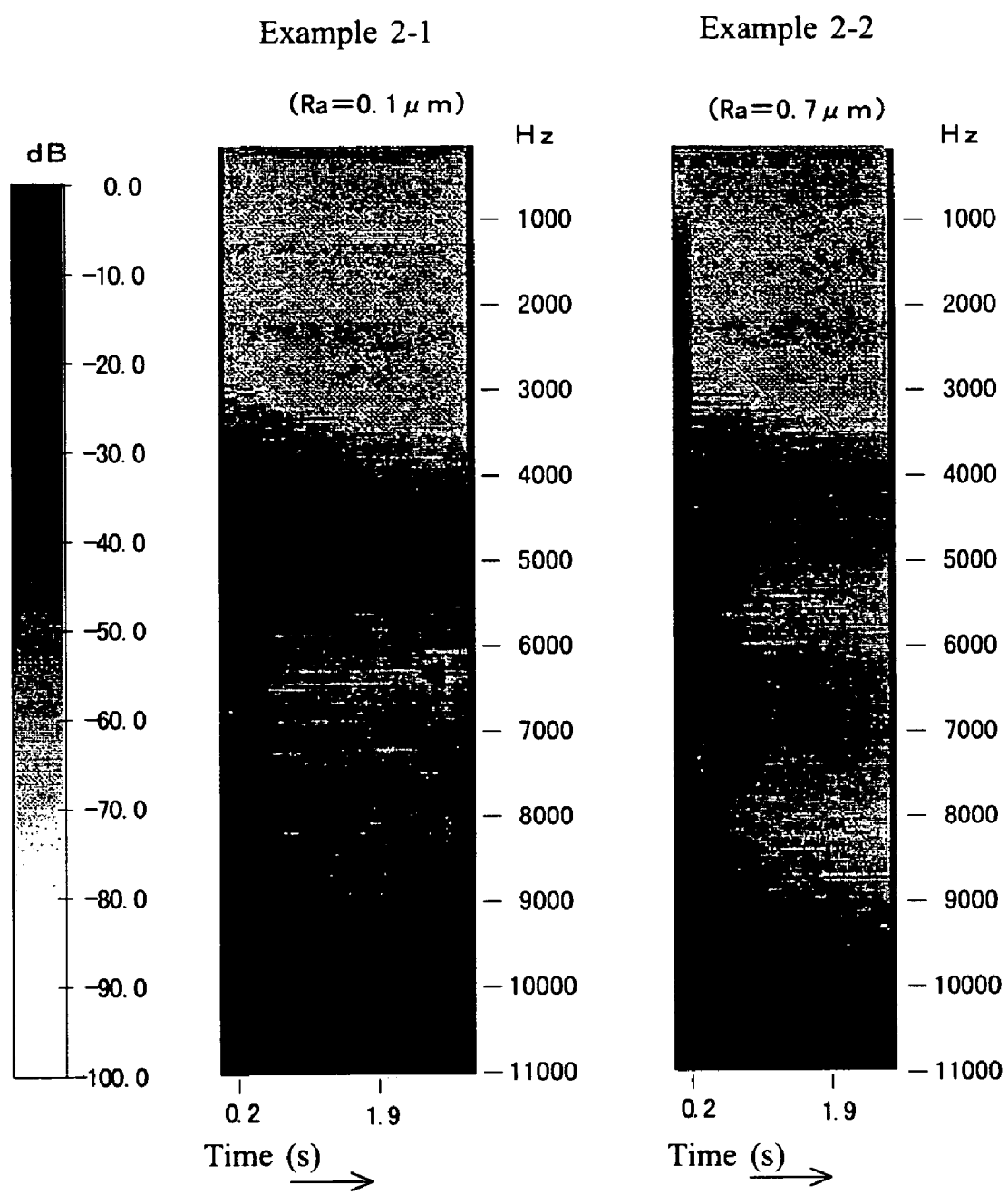
FIG. 13 is a graph of a measured sliding sound.

(3) Surface Roughness of a Sliding Element and Detection Characteristics of a Sliding Sound Each of the hair sensors of Examples 2-1 and 2-2 was run through the hair sample used in (2) and the sliding sound was measured. FIG. 13 is a graph showing a temporal change of a power spectrum obtained by a frequency analysis of the sliding sound. FIG. 13 shows that a strong sliding sound was detected in two frequency bands (a band around 5500 Hz and a band around 8000 Hz) in Example 2-2 in which the surface roughness was 0.7 µm. By contrast, in Example 2-1 in which the surface roughness was 0.1 µm, a sliding sound around 6000 Hz was clearly stronger although a sliding sound around 9000 Hz was not clear. Therefore, the sensitivity is higher in the hair sensor of Example 2-2 in which the surface roughness of the sliding element was rougher, than in the hair sensor of Example 2-1.

Similar results were also obtained in the case of using a bundle of blond hair as a hair sample.

(4) Comparison of Sliding Sounds Based on Characteristics of Hair

A bundle of chemically untreated straight hair of an Asian used in (2), a bundle obtained by bleaching that bundle, and a bundle of Asian hair containing frizzy hair were prepared. For each of the hair bundles, a sliding sound was measured by means of the hair sensor of Example 2-2. Bleaching was performed by using a bleaching agent obtained by mixing Liquid 1 and Liquid 2 of Lavenus Color Appeal Bee High Bleach, available from Kao Corporation, at a ratio of 2:3. A process in which the same weight of this bleaching agent as the weight of the hair sample was applied onto the hair sample for 20 to 30 minutes at room temperature was repeated. FIGS. 14, 15A, 15B, and 15C show the measurement results.

Figure 14:
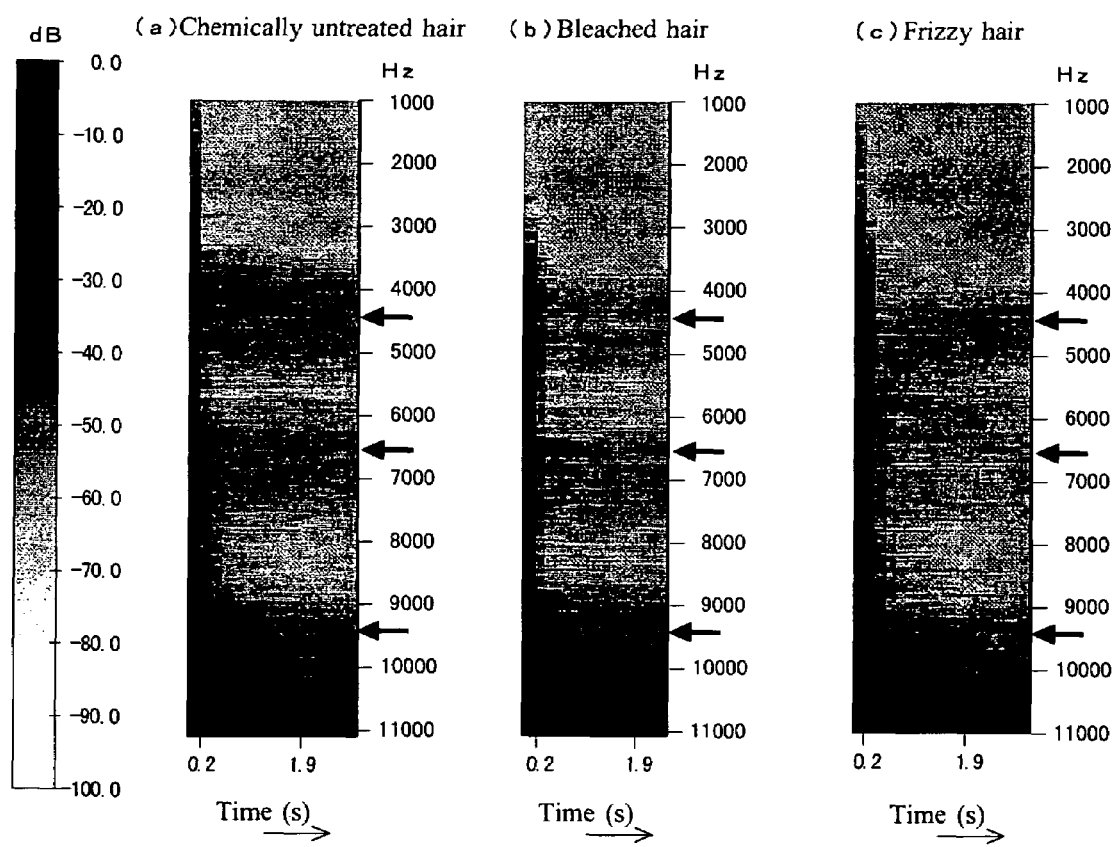
FIG. 14 is a graph of a measured sliding sound.
Figure 15A:
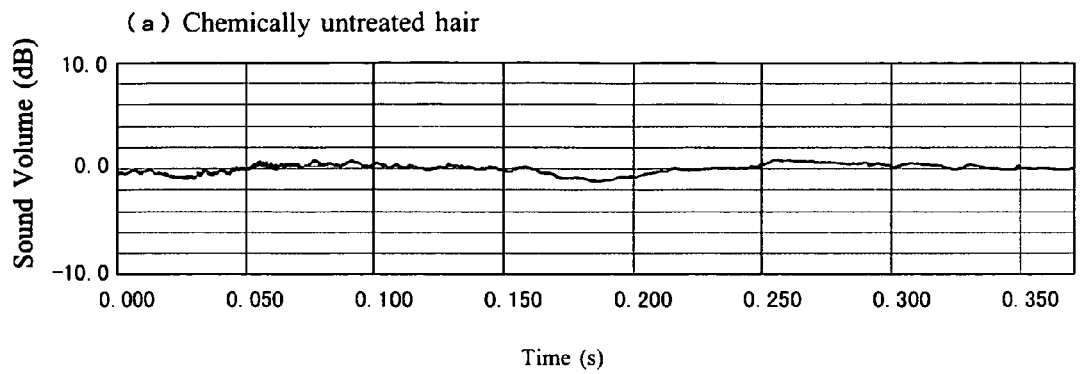
FIG. 15 is a graph of a measured sliding sound.
Figure 15B:
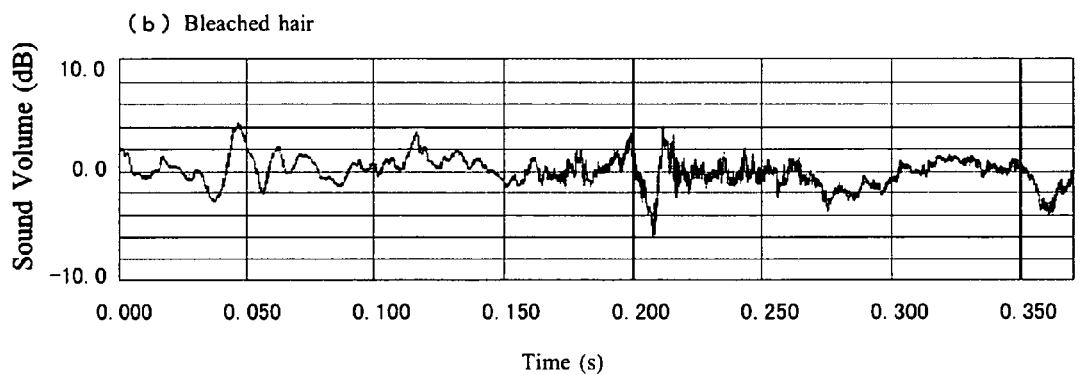
Figure 15C:
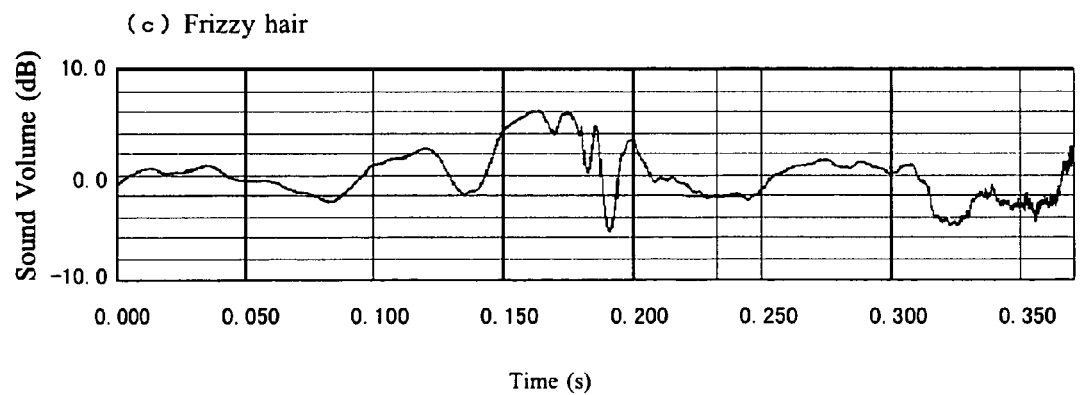

It is shown from FIG. 14 that the sliding sound of the bleached hair was stronger than that of the chemically untreated hair before bleaching at frequencies of 4000 Hz or more. It is also shown that the intensity of the sliding sound of the hair containing the frizzy hair was strong over a wide frequency band and the noise level was high especially at frequencies of 4000 to 5000 Hz, 6000 to 7000 Hz, and 9000 to 10000 Hz in the sliding sound of the hair containing the frizzy hair.

Moreover, it is shown from FIG. 15 that the intensity of the sliding sound of the chemically untreated hair before bleaching was totally low whereas high frequency components appeared after bleaching and that the sliding sound of the hair containing the frizzy hair contained low frequency components (large undulation).

Example 3

A hair sensor was fabricated in the same manner as that in Example 2-2, except that a strain gauge 15 was provided on the back of the diaphragm 12, as shown in FIGS. 9A and 9B. In this case, a strain gauge FLA-2-11-1L manufactured by Tokyo Sokki Kenkyujo Co., Ltd. was used as the strain gauge 15 and was bonded to the back of the diaphragm 12 with an adhesive glue available from that corporation exclusively. A signal detected by the strain gauge was amplified by an amplifying circuit for a strain gauge and was then inputted to a personal computer as an analog signal. In this manner, a load applied on hair when the hair sensor was run through the hair, and the sliding sound were measured simultaneously.

Figure 16A:
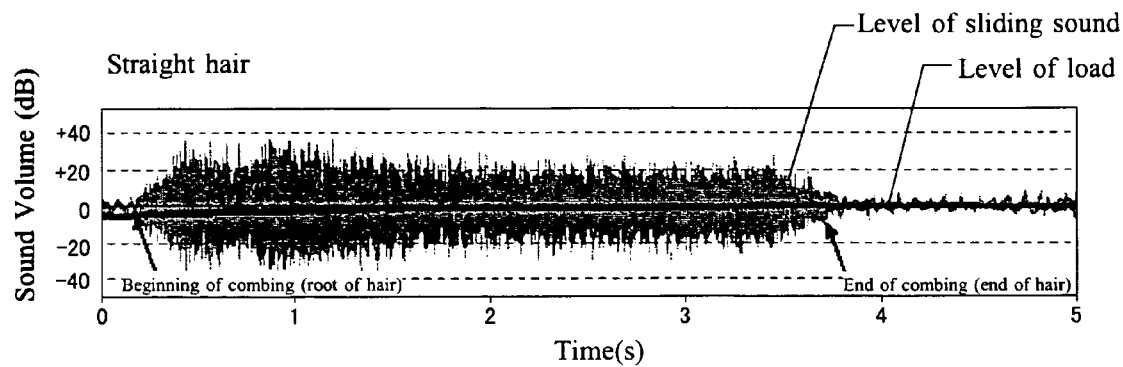
FIG. 16A is a graph of a sliding sound and a load that were measured.
Figure 16B:
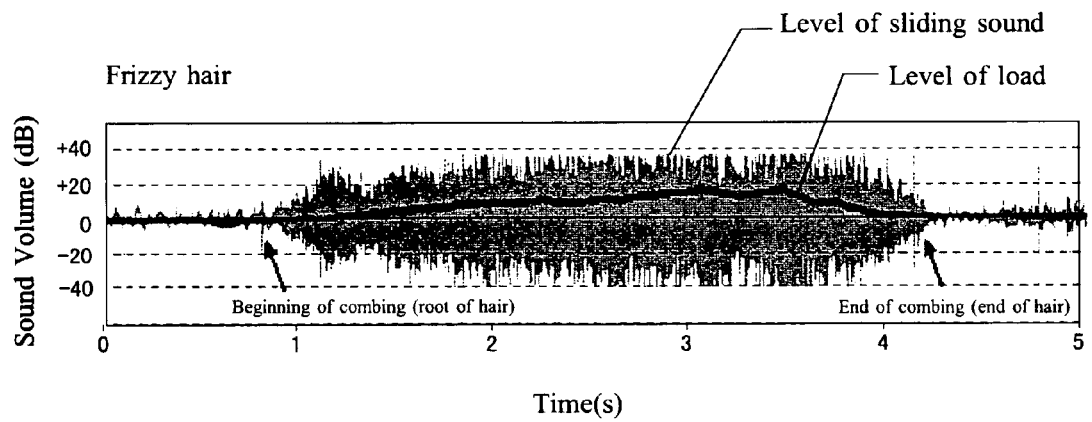
FIG. 16B is a graph of a sliding sound and a load that were measured.

With this hair sensor, the sliding sound and the load when the hair sensor was run through each of the hair sample of Asian straight hair and the hair sample containing frizzy hair that were used in Example 2(4) were measured. FIGS. 16A and 16B show the measurement results.

It is shown from FIGS. 16A and 16B that the load and the sliding sound were constant from the beginning to the end for the hair sample of straight hair. On the other hand, it is shown that the load and the sliding sound became larger toward the end of the hair for the hair sample containing frizzy hair. Please note that hair on which a large load is applied tends to generate a large sliding sound.

In hair for which a large load is measured, split ends or breakages of hair can easily occur because of daily brushing. Therefore, it is possible to find a site at which split ends or breakages of hair can easily occur by measuring the load.

Example 4

A detection system for detecting a sliding sound shown in FIG. 20B was formed by incorporating CM108 (LSI chip), available from C-Media Electronics Inc., into a housing 2 of a hair sensor 1 shown in FIGS. 1A and 1B. In the detection system, an amplifier 21 was not used and the hair sensor 1 was directly connected to a personal computer 23 via a USB connector. CM108 had a function of processing an audio signal and a function of a USB interface. Moreover, a capacitor of 0.022 µF as a low-frequency noise filter was connected to a decoupling capacitor in series.

Figure 17A:
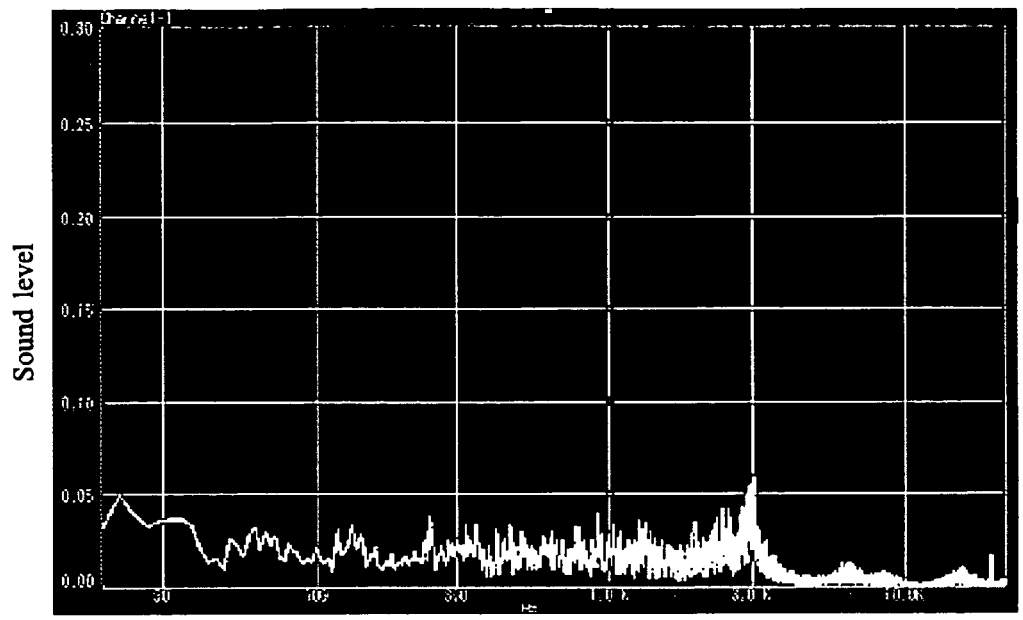
FIG. 17A is a graph of a measured sliding sound when using a hair sensor including a low-frequency noise filter.
Figure 17B:
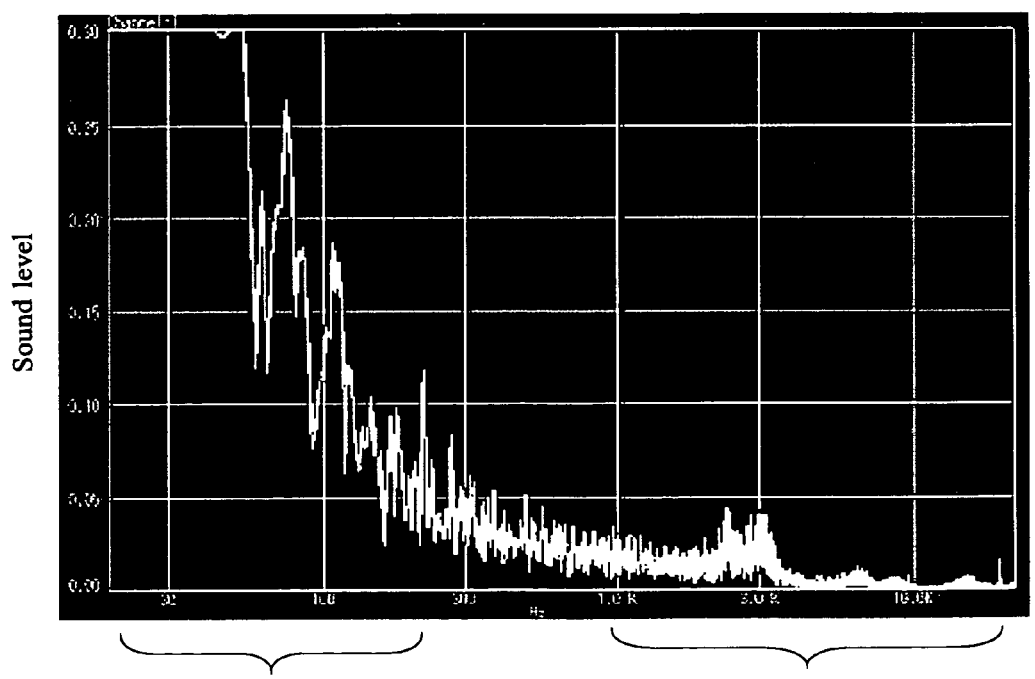
FIG. 17B is a graph of a measured sliding sound when using a hair sensor including no low-frequency noise filter.

With this hair sensor, a sliding sound was measured for a hair sample of Asian straight hair used in Example 2(2). In addition, a hair sensor that was the same as the above hair sensor except that the capacitor of 0.022 µF as the low-frequency noise filter was not provided was manufactured. With this hair sensor, measurement of the sliding sound was performed in a similar manner. FIGS. 17A and 17B show the measurement results.

In FIG. 17B (showing a case where no low-frequency noise filter was provided), a strong signal at frequencies of 300 Hz or less represents low-frequency sounds generated when an operator grasps the hair sensor or during the measurement.

On the other hand, in FIG. 17A (showing a case where the low-frequency noise filter was provided), it is confirmed that the low-frequency sound was suppressed to a low level and therefore the sliding sound could be observed without an unwanted noise sound. More specifically, a filtering effect of approximately −20 db or more was found at frequencies of 50 Hz or less and a loss within approximately −3 db was found at frequencies of 300 Hz or more. The above effects achieved by the low-frequency noise filter are significant when an operator or an examinee hears the measuring sound by ear. Without the filter effect the sliding sound is hidden in the low-frequency sounds and is hard to hear.

According to a hair sensor of the present invention, a sliding sound of hair can be detected while noise detection is suppressed to a minimal level. Thus, it is possible to easily and accurately estimate hair characteristics from the detected sliding sound. Therefore, the hair sensor of the present invention can be used for counseling on a hair condition or a test for effects of a hair care product, or as a tool supporting sales of a hair care product, for example.

The entire disclosure of the specification, claims, summary and drawings of Japanese Patent Application No. 2005-016199 filed on Jan. 24, 2005 is hereby incorporated by reference.

What is claimed is:

1. A hair sensor for detecting a sliding sound of hair in order to estimate hair characteristics, comprising:
   a sliding element capable of sliding on hair;
   a housing including a microphone provided therein;
   a diaphragm on which the sliding element is located to erect, wherein the sliding element and the diaphragm are arranged to allow a sliding sound caused by the sliding element to be transmitted to the microphone as vibration and to attenuate vibration transmitted from outside of the diaphragm to the microphone; and
   the diaphragm is configured so as to be in direct contact with said microphone so as to allow a sliding sound caused by the sliding element to be transmitted to the microphone as a vibration.

2. The hair sensor according to claim 1, further comprising a vibration attenuator for attenuating the vibration transmitted from the outside of the diaphragm to the microphone, the vibration attenuator surrounding the microphone except for a position at which the diaphragm is located.

3. The hair sensor according to claim 1, wherein the sliding element comprises a plurality of bar-like sliding elements.

4. The hair sensor according to claim 3, wherein the sliding element comprises flat-bar-like sliding elements arranged in a line in a thickness direction of the flat-bar-like sliding elements.

5. The hair sensor according to claim 3, further comprising a guard member provided on both sides of the bar-like sliding elements in such a manner that the guard member projects from the bar-like sliding elements to prevent the bar-like sliding elements from coming into contact with a scalp.

6. The hair sensor according to claim 3, wherein the bar-like sliding elements are located to extend from the diaphragm integrally formed with the bar-like sliding elements.

7. The hair sensor according to claim 1, wherein the sliding element is formed of a metal material that is surface-treated to have a rough surface.

8. The hair sensor according to claim 1, wherein the housing is bent around a top end thereof and the sliding element is provided at the top end of the housing so as to be replaceable.

9. The hair sensor according to claim 1, further comprising a strain gauge connected to said microphone to detect a load applied to the hair for analysis of a condition of the hair.

10. The hair sensor according to claim 1, being capable of being connected to a computer via a USB (Universal Serial Bus).

11. The hair sensor according claim 1, wherein the attenuator comprises a low-frequency noise filter for suppressing a low frequency component.

12. The hair sensor according to claim 1, wherein the sliding element has a surface roughness of from 0.1 μm to 5.0 μm.

13. The hair sensor according to claim 11, wherein the attenuator low-frequency noise filter has a filtering effect of −12 db or more.

14. The hair sensor according to claim 1, wherein said microphone comprises a cardioid microphone for noise suppression.

15. The hair sensor according to claim 5, wherein said guard has a greater length than said sliding element so as to prevent contact of an end portion of said sliding element with a scalp of an individual.

* * * * *